United States Patent [19]
Salcudean et al.

[11] Patent Number: 5,382,885
[45] Date of Patent: Jan. 17, 1995

[54] MOTION SCALING TELE-OPERATING SYSTEM WITH FORCE FEEDBACK SUITABLE FOR MICROSURGERY

[75] Inventors: Septimiu E. Salcudean; Joseph Yan, both of Vancouver, Canada

[73] Assignee: The University of British Columbia, Vancouver, Canada

[21] Appl. No.: 103,653

[22] Filed: Aug. 9, 1993

[51] Int. Cl.⁶ ............................................. G05B 11/00
[52] U.S. Cl. .......................... 318/568.11; 318/568.1; 318/568.21; 901/9; 395/99
[58] Field of Search ............................... 318/560–646; 901/1, 3, 5, 7, 9, 12, 13, 15, 18, 20, 23; 395/80–99; 414/730–735

[56] References Cited

U.S. PATENT DOCUMENTS

| | | | |
|---|---|---|---|
| 4,661,032 | 4/1987 | Arai | 318/568 |
| 4,874,998 | 10/1989 | Hollis, Jr. | 318/568.21 |
| 4,887,222 | 12/1989 | Miyake et al. | 901/2 |
| 4,897,586 | 1/1990 | Nakata et al. | 318/568.1 |
| 5,023,533 | 6/1991 | Ishikawa et al. | 318/568.21 |
| 5,105,367 | 4/1992 | Tsuchihashi et al. | 395/99 |
| 5,116,180 | 5/1992 | Fung et al. | 901/9 |
| 5,146,566 | 9/1992 | Hollis, Jr. et al. | 395/275 |
| 5,266,875 | 11/1993 | Slotine et al. | 318/568.11 |

OTHER PUBLICATIONS

J. W. Hunter "A Microrobot for Manipulation and Dynamical Testing of Single Living Cells" Proc. IEE Microelectro Mechanical System pp. 102–106 Feb. 1989.

R. L. Hollis et al. "Towards a Telenano Robotic Manipulation System with Atomic Scale Force Feedback and Motion Resolution" Proc. 3rd IEEE Microelectro Mechanical Systems pp. 115–119 Feb. 1990.

Mastogaa-Sharzewski "A Master Slave Manipulator for Exclavation and Construction Tasks" Robotics and Autonomous System 4.333–337, 1989.

Lavellee "Image Guided Operating Robot, a Clinical Application in Stereotactic Neuro Surgery" IEEE International Conference on Robotics & Automation, pp. 618–624 May 10–15, 1992.

Paul "A Surgical Robot for Total Hip Replacement Surgery" IEEE International Conference on Robotics and Automation pp. 606–611 May 10–15, 1992.

Kozanzides "Force Sensing and Control of a Surgical Robot" IEEE International Conference on Robotics & Automation pp. 612–617 May 10–15, 1992.

Hollis "Six Degree of Freedom Magnetically Levitated Variable Compliance Fine Motion Wrist" Design, Modeling, and Control, IEEE Transaction on Robotics & Automation 7(3) 320–322 Jun. 1991.

Sacludean "A Force Reflecting Teleoperation System with Magnetically Levitated Master and Wrist" Proceeding IEEE International Conference on Robotics & Automation May 10–15, 1992.

McEwen "Solo Surgery with Automated Positioning Platforms" New Frontiers in Minimally Invasive and Interventional Surgery Oct. 13, 1992.

*Primary Examiner*—Paul Ip
*Attorney, Agent, or Firm*—C. A. Rowley

[57] ABSTRACT

A robot suitable for micro-surgical application is formed by a robot arm having a position adjustable free end on which are mounted with their respective stators in fixed relationship a master and a slave robot. The position and actuation of the moving element of the master (master floater) and the moving element of the slave (slave floater) are used to couple their moment such that the master floater motion and forces are scaled down and followed by the slave and the slave floater motion and forces are scaled up and followed by the master. The sensed environment forces on the slave floater and sensed hand (environment) forces on the master can be used to improve the coordination between the master and the slave.

19 Claims, 4 Drawing Sheets

MOTION SCALING TELE-OPERATING SYSTEM WITH FORCE FEEDBACK SUITABLE FOR MICROSURGERY

FIELD OF THE INVENTION

The present invention relates to a robot arm having macro-position adjustment and micro-position adjustment.

BACKGROUND OF THE PRESENT INVENTION

Microsurgery involves tasks that require dexterity levels beyond the normal range of unaided human abilities including motions as small as a few microns and applied forces as delicate as a few grams. Microsurgery operations commonly require up to three hours of intense work that is usually performed after several hours of routine procedure and so it follows reasonably that fatigue and frustration are significant problems for the microsurgeon.

Teleoperation is well known and is used as a way to extend the human reach into hostile or distant environments and has recently started to encompass the extension of human reach through barriers of scale to allow, for example, a person to work on an individual living cell as described by I. W. Hunter et al. in an article entitled, "A Microrobot for Manipulation and Dynamical Testing of Single Living Cells" in Proc. IEEE Microelectro Mechanical Systems, pp 102–106, Salt Lake City, February 1989 or to feel an atom surface, see R. L. Hollis et al., "Towards a Telenano Robotic Manipulation System with Atomic Scale Force Feedback and Motion Resolution", in Proc. 3rd IEEE Microelectro Mechanical Systems, pp 115–119, Nappa Valley, Calif., February 1990 or the other extreme, to feel the payloads of an excavator, see Mostogaa-Starzewski et al., "A Master Slave Manipulator for Excavation and Construction Tasks"; in Robotics and Autonomous Systems, 4:333–337, 1989.

A fine motion technology known as Lorentz magnetic levitation which provides six degrees of freedom (6 DOF) limited range friction less motion with programmable compliance has been applied to a magnetically levitated (maglev) robot wrist as described in Hollis U.S. Pat. No. 4,874,998 issued October 1989, the disclosure of which is incorporated herein by reference and further amplified in a paper by Hollis et al., "Six Degree of Freedom Magnetically Levitated Variable Compliance Fine Motion Wrist", Design, Modelling and Control, IEEE Transactions on Robotics and Automation, 7(3):320–332, June 1991.

A force reflecting system compatible with the above described fine motion technologies described by Salcudean et al. in "A Force Reflecting Teleoperation System with Magnetically Levitated Master and Wrist" in Proceedings of the IEEE International Conference on Robotics and Automation, Nice, France, May 10–15, 1992.

A number of applications of robotics which were used in the medical field have been described in the art, see for example; James McEwen, "Solo Surgery with Automated Positioning Platforms" in Proceedings of the New Frontiers in Minimally Invasive and Interventional Surgery, New Orleans, La., Oct. 13, 1992; Lavalee et. al in "Image Guided Operating Robot, a Clinical Application in Stereotactic Neuro Surgery" in Proceedings of the IEEE International Conference on Robotics and Automation, pp 618–624, Nice, France, May 10–15, 1992; Paul et al. in "A Surgical Robot for Total Hip Replacement Surgery" in Proceedings of the IEEE International Conference on Robotics and Automation, pp 606–611, Nice, France, May 10–15, 1992; and, Kazanzides et al. in "Force Sensing and Control of a Surgical Robot" in Proceedings of the IEEE International Conference on Robotics and Automation, pp 612–617, Nice, France, May 10–15, 1992.

BRIEF DESCRIPTION OF THE PRESENT INVENTION

For the purposes of the disclosure and claims the term "stator" is intended to describe the base or normally fixed portion of the master or slave of the robot or micro teleoperation system and the term "floater" is intended to mean the moveable portion of the robot or micro teleoperation system. And the robot or micro teleoperation system may be any suitable master/slave combination such as parallel drive mechanisms known as "Stewart platforms", but maglev floaters are preferred.

It is an object of the present invention to provide a motion scaling telerobotic system wherein the surgeon may accurately control minute movements of an instrument while feeling scaled-up forces representative of the forces applied on the tool.

Broadly, the present invention relates to a robot comprising an arm having a position adjustable-free end, said arm having joint connections constructed for macro-adjustments of said free end, an extension mounted on said free end, said extension forming part of a micro-movement robot or micro teleoperation system having in fixed relationship a slave stator and a master stator, a slave moving element (slave floater) cooperating with said slave stator and a master moving element (master floater) cooperating with said master stator, means for sensing the position of each of said master and said slave floaters relative to their respective said master and said slave stators, coupling means coupling said master floater and said slave floater in a manner so that movement of said master floater produces a scaled moment of said slave floater and moment of said slave floater produces a scaled movement of said master floater, said moment of said master resulting in a significantly smaller corresponding scaled movement of said slave floater and said movement of said slave resulting in significantly larger corresponding scaled movement of said master floater.

Preferably said coupling means will include a programable computer means to scale said corresponding scaled movements of said master and slave floaters in accordance with a selected program.

Preferably, said robot will further comprise means for sensing forces applied to said slave floater from its environment.

Preferably said robot will further comprise means for sensing forces applied to said master floater by its environment.

Preferably said coupling means further comprise means for modifying sensed slave and said master environment forces and means for applying said modified forces to said master and said slave floaters respectively.

Preferably said coupling means will include a programable computer means to scale said corresponding movements of said master and said slave floaters and said sensed forces in accordance with a preselected program and wherein said motions and forces are implemented for transparency in accordance with appropriate programmed processing of said master and said slave floater positions and sensed slave and master environment forces.

Preferably, computer-assisted means will be provided for controlling the compliance of the master and/or slave to guide the movement of the master and/or slave.

Preferably, means will be provided to manually over ride motion scaling of the master to the slave.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
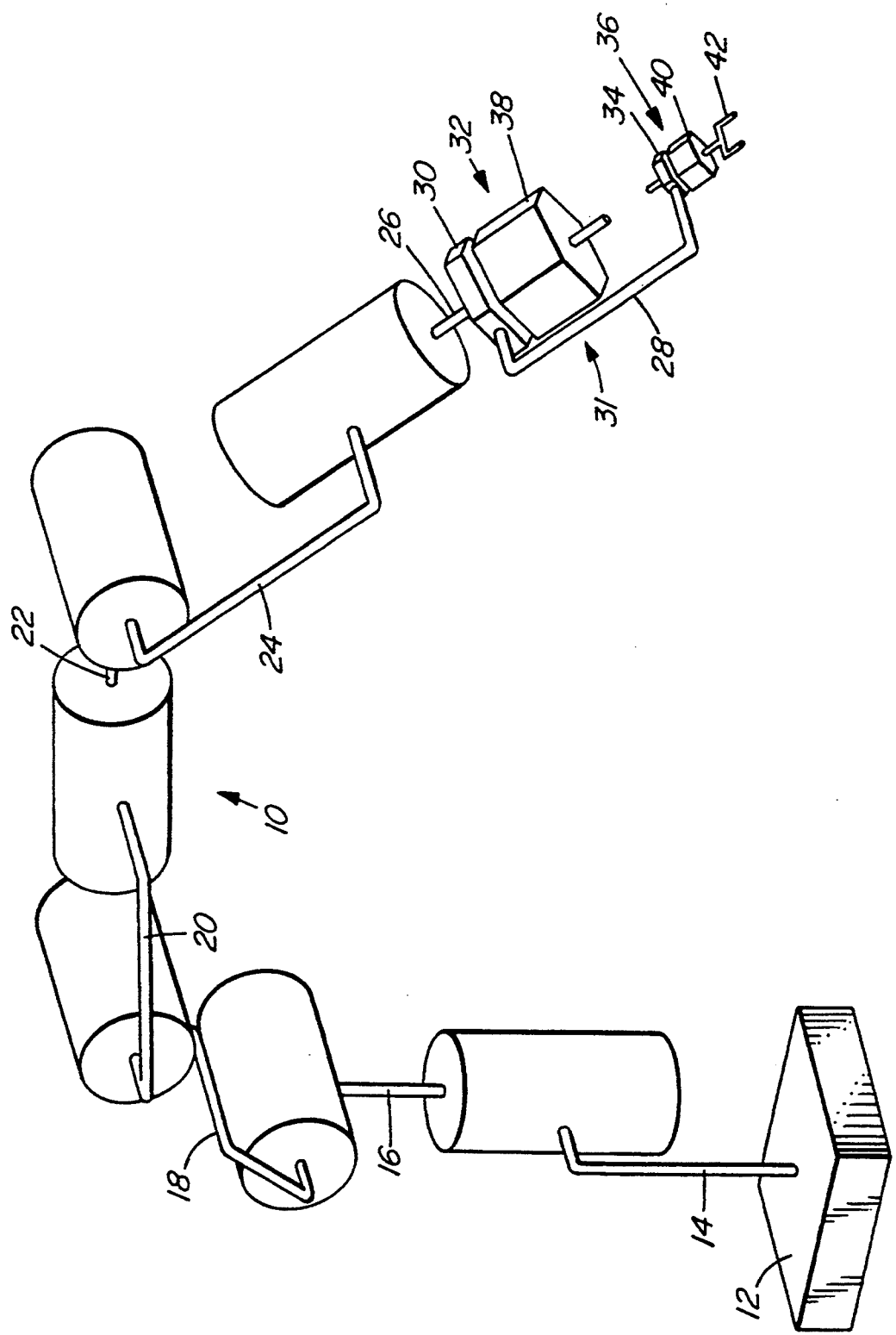
FIG. 1 is a schematic representation of the present invention with a coarse motion transport arm having a master and a slave mounted on its free end.

In the embodiment of the invention shown in FIG. 1, the arm of the present invention includes a coarse motion or macro-motion robot arm 10 composed of a plurality of different links which in the illustrated arrangement, include a base 12 first link 14, second link 16, third link 18, fourth link 20, fifth link 22, sixth link 24 and a seventh link 26, which forms part of the free end extension 28 that forms a common base 28 for a robot or micro teleoperation system 31.

Obviously the macro-motion manipulator arm may have any suitable configuration and is not intended to be limited to the arrangement schematically illustrated. While the coarse motion arm 10 has been indicated as an elbow-type manipulator with wrist actions or some form of pivotal actions, it will be apparent that other transport mechanisms could be used, for example, Stewart platforms to permit the coarse manipulation of the extension 28 at the free end of the arm 10.

A counterbalanced coarse robot or manipulator arm with at; least six degrees of freedom is the preferred construction wherein the centres of mass of the arm sections do not change significantly with changes in configuration and little or no power consumption is required to hold the arm 10 in position. As will be described below the coarse robot 10 must be easily back-driveable so that the system may easily be moved out of the way.

The base 28 of the robot or micro teleoperation system 31 forms a common base for the "stator" 30 of the master 32 and the "stator" 34 of the slave 36 which form the master/slave combination of robot or micro teleoperation system 31. The master 32 has a "floater" 38 that is coupled (as will be described herein below in conjunction with FIG. 4 ) via the computer system 90 to govern the movement of the "floater" 40 of the slave 36.

The slave 36 is provided with a suitable mounting means for holding a tool, such as the tool schematic illustrated at 42.

The robot or micro teleoperation system 31 may be any suitable robot incorporating a master/slave relationship, but the preferred form will be a magnetic levitation employing system for the master and slave.

Figure 2:
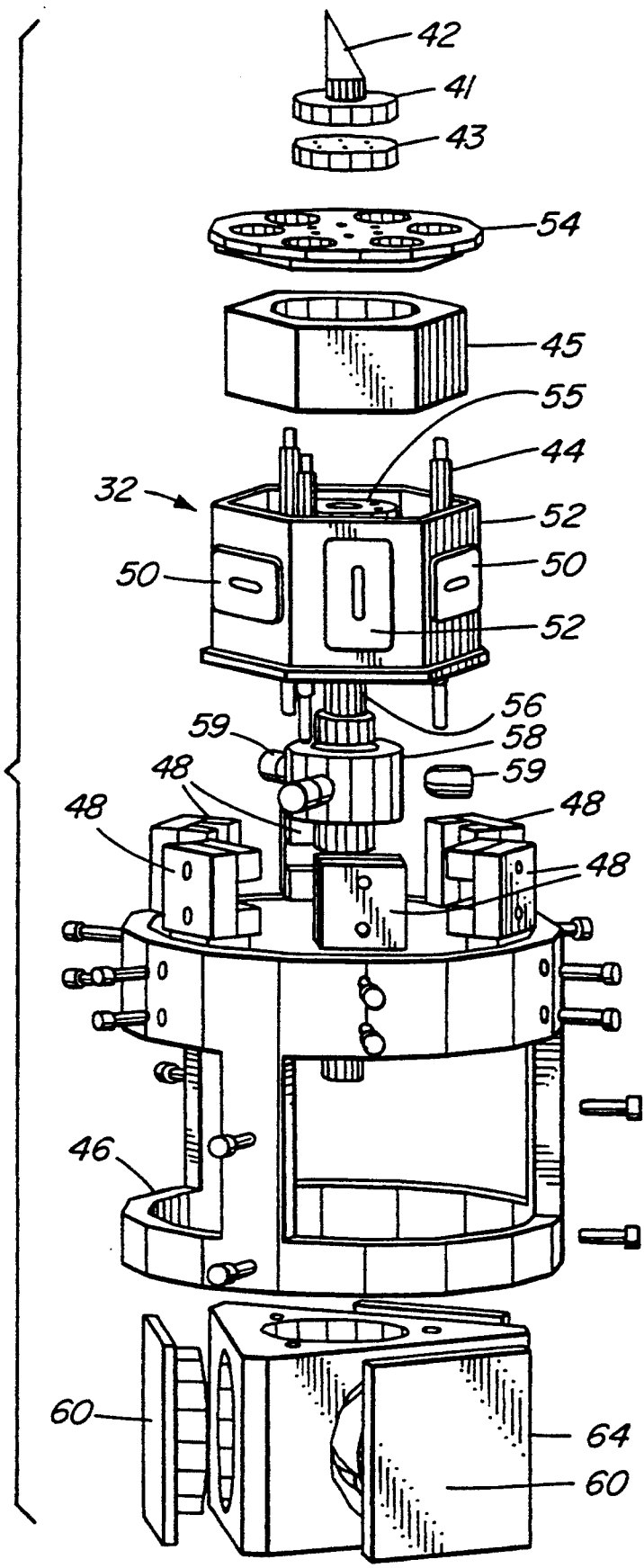
FIG. 2 is an exploded view of an assembly representing one embodiment of either a slave manipulator or a master manipulator (with certain obvious modifications).

One suitable form of maglev slave 36 or master 32 manipulator for the robot 31 is shown in exploded view in FIG. 2. Actuator illustrated being a slave since it is provided with an instrument or tool 42 mounted thereon by a suitable mounting schematically indicated by the flange 41 which preferably will include a force and torque sensor 43 interposed between the mounting flange 41 and the floater 38 as will be described below. The master and slave may be built essentially the same but to a different scale.

A suitable construction of the master 32 and slave 36 is disclosed in U.S. Pat. No. 4,874,998, referred to above.

To further describe the master and slave systems, the stator (30 or 34) includes the stator iron core 45 mounted on the support rods 44 from the stator support ring 46 which also mounts in uniformly circumferentially spaced relationship around the axis of the manipulator, a plurality of peripheral stator magnetic assemblies 48. In the illustrated arrangement, there are six such magnetic assemblies 48 that cooperate with the correspondingly positioned floater coils 50 mounted on the floater core 52 (floaters 38 and 40). These floater coils 50 are flat spirally wound coils arranged with the major axes of adjacent coils 50 substantially perpendicular as illustrated. In the illustrated arrangement the coils 50 are positioned on the faces of a hexagonal cross sectional cylinder core 52.

The floater core 52 on which the floater coils 50 are mounted is secured to a floater top 54 which is fixed to a floater shaft 56 by any suitable means (in the illustrated arrangements) by bolts not shown, passing through holes of the floater top 54 and threaded into an end cap 55 of the shaft 56.

Mounted between the floater top 54 and the mounting flange 41 of the interchangeable tool 42 there preferably is positioned a force and torque sensor 43 referred to above which senses the forces applied to floater 40. This sensed information is delivered to the computer system 90 (as will be described in discussing FIG. 4) via suitable connections not shown.

Mounted on the shaft 56 is the position sensor 58 for determining the location and orientation of the floater 38 or 40. The floater portion of the position sensor 58 mourns three symmetrically positioned light emitting diodes (LEDs) 59 which project light onto the surfaces of their respective two dimensional position sensing diodes (PSD), one for each LED, but only two which are schematically illustrated in FIG. 2 at 60 as forming part of the stator PSD assembly 64 which is fixed to the stator support ring 46. Calculations using the three pairs of coordinates generated by the light being sensed on the stator PSDs 60 are used to generate position and orientation of the floater (38 or 40) with respect to the stator (30 or 34) in both the master 32 and slave 36.

Figure 3:
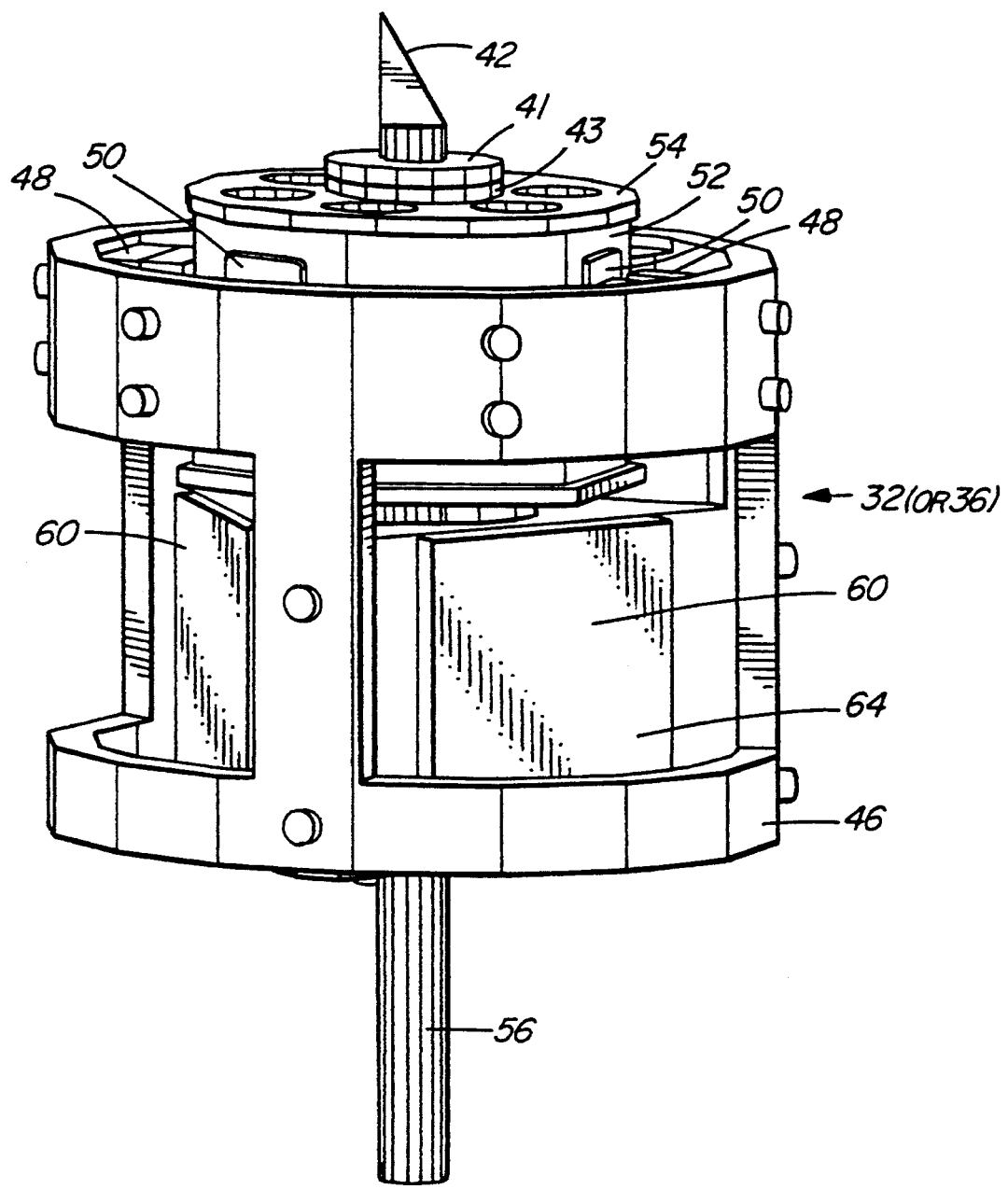
FIG. 3 is an assembled slave manipulator with a tool mounted therein.

The assembled unit is illustrated in FIG. 3 with the tool 42 mounted thereon, and thus illustrates a slave as opposed to a master, however, the master 36 can be essentially the same.

The coarse motion stage arm 10 must compensate for the weight of the extension 28 carrying the master 32 and slave 36 mounted thereon and must be back drivable when the arm 10 is operating in the active (computer controlled) or passive modes and easily over ridden by the surgeon for example by manipulation of the master beyond the range of movement of the master floater 38 relative to the master stator 30.

The control system 90 (see FIG. 4) uses the sensed positions of the master and slave floaters relative to their respective stators to control the operation of the system so that the slave floater mimics the motion of the master floater and vice-versa, the motion of the master floater mimics the motion of the slave floater. Such "coordinated motion" will provide force feedback such that the forces exerted by the environment on the slave floater, and vice versa the forces exerted by the slave floater on the environment mimic those exerted by the hand (surgeon's hand or the environment) on the master. Further use of the sensed environment forces on the slave floater by the sensor 43 and or the sensed hand forces on the master floater by thew equivalent sensor in the master can be used to improve the motion coordination between the master and slave floaters and the fidelity with which the master and slave floaters mimic the forces exerted on each other using well known techniques.

In the case where an active positioning robot 10 is used the control system 90 also coordinates the motion of the coarse robot 10 with the motion of the master and slave floaters by (as will be described below) directing the motion of the stator base 28 to track the master floater 38 or the slave floater 40 whenever the master floater or the slave floater is near the edge of its workspace, thus allowing the operator (surgeon) to position the tool within a large workspace.

The controller can also be used to vary compliance of the master and slave in a preprogrammed manner so that motion control can be "shared" between the operator (surgeon) and the computer. For example, the computer may guide the direction of a cut while the surgeon may control the depth and speed of the cut.

Figure 4:
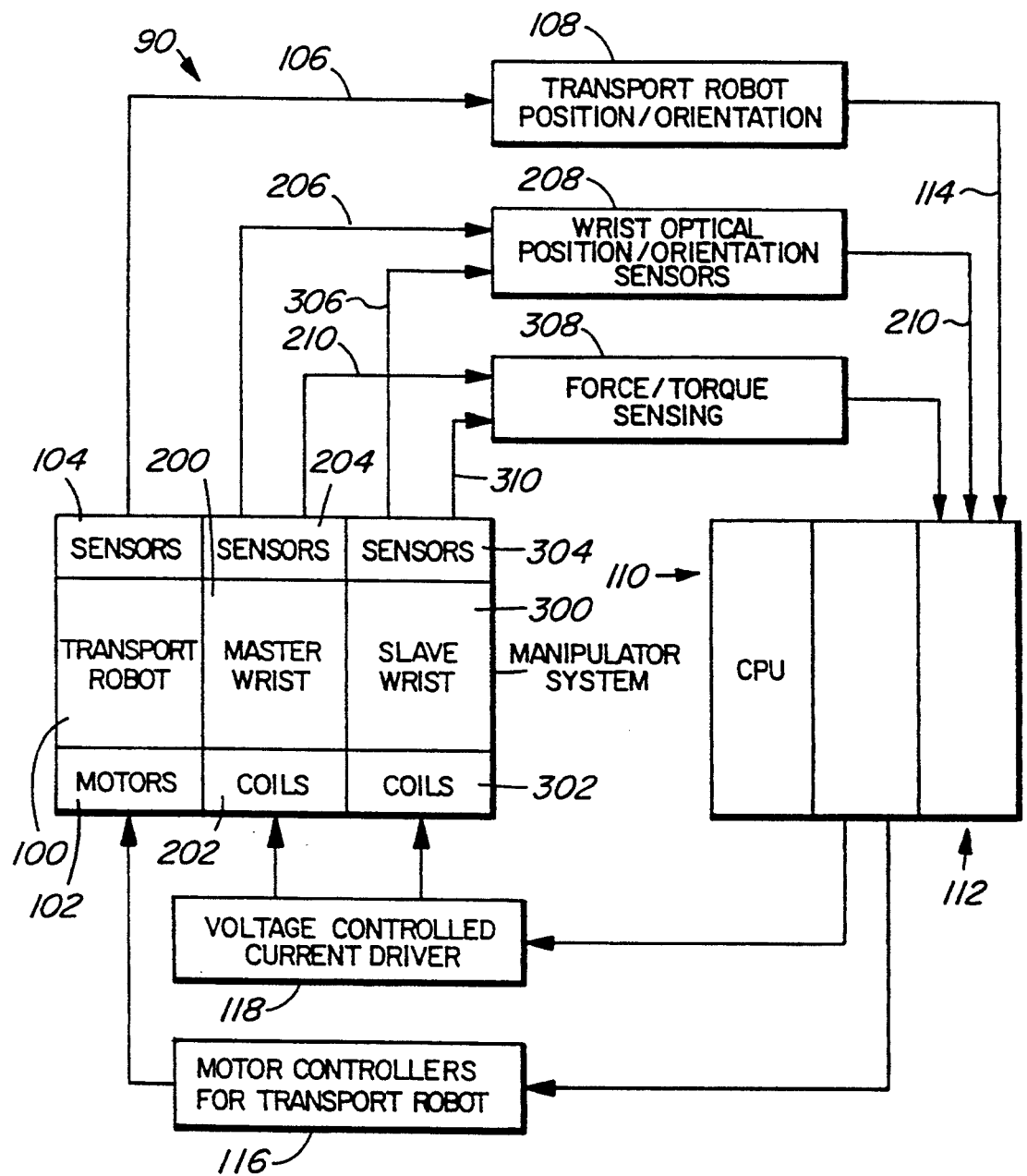
FIG. 4 is a schematic representation of a computer control system suitable for use for the present invention.

As illustrated in FIG. 4, the coarse transport system (arm 10) schematically indicated at 100 when it is used in the active mode to control the position of the extension 18 is provided with robotic controls which normally include, for example, cylinders or magnetic devices functioning as controllable motors as indicated at 102 and with sensors as indicated at 104 to indicate the relative positions and orientations of the various links 14, 16, etc,. of the arm 10 of the coarse transport system 100 so that its positioning can be defined, i.e. the position of the extension 28. The sensors 104 provide signals designating the location of the various arms via line 106 to a transport robot position orienting and sensing system 108 which feeds this information to the central processing unit or computer generally indicated at 110. The position and orientation system 108 feeds a signal to the central processing computer unit 110.

The master wrist control (master 32) as schematically indicated at 200, includes drive coils (floater coils 50) 202 used to position the master 32 (floater 38) and position sensors 204 (formed by the assemblies 58 and 64) to sensed the position of the master floater 38 and deliver this information via line 206 to the master optical position and orientation system 208 which feeds this information to the central processing unit 110 in as indicated by the line 210.

The slave manipulator system is essentially the same as that of the master and as schematically indicated at 300 is provided with coils (floater coils 50) 302 which position the slave 36 (i.e. the slave floater 40) and with position sensors 304 (formed by the assemblies 58 and 64) that sense the position of the floater 40 of the slave 36 and feed this information via line 306 to the same positioning and orienting sensor station 208 as used for the master.

The master 32 (floater 38) and slave 36 (floater 40) are controlled so that the movements of the master floater 38 are mimicked by the slave floater 40 and vice versa, but with a scaling factor reducing the movements of the slave relative to the corresponding moments of the master. Thus if the master floater 38 is manipulated a corresponding, but down scaled (smaller) moment of the slave floater 40 is produced. Similarly if the slave floater 40 is moved a corresponding but up-scaled (lager) movement of the master floater 38 is produced.

The sensors 304 for the slave wrist 36 may further include the force sensors in the head 55 that sense forces applied via the environment, i.e. the forces that resist movement of the tool 40 are schematically represented by the force and torque sensing unit 308 connected via the line 310.

In the illustrated arrangement, the master controller 100 is also provided with force and torque sensors schematically represented by the force and torque sensing station 308 connected via line 310.

The master force sensor 43 measures the forces exerted on the master floater by the operator (surgeon).

Whether the macro-movement arm 10 is passive a system or an active system when the master 32 or slave 36 is being manipulated beyond a selected maximum displacement of the master 32 or slave 36 this moment may be applied to move into the macro-movement mode.

It is important that the surgeon or operator be able at any time to manually override and assume full command of the system for example to manipulate the tool 42 manually. This may be accomplished, for example, by locking the master floater to the slave floater with no scaling i.e. programming the scaling factor to 1, however, this may be difficult to accomplish quickly. Preferably the system is constructed so that the slave floater 40 may be directly manipulated by the operator (surgeon) by griping the floater 40 of the slave 38 and directly control the movement of the tool 42. Obviously direct manipulation of the tool 42 requires that the remainder of the system track the operator's hand (tool motion) to permit this manipulation as required by the operator.

Preferably the coarse fine motion coordination i.e. backdriving the coarse motion arm 10 from the master or slave floaters 38 or 40 respectively will be based on position information the master. The master control will be programmed to have a deadband zone wherein motion of the master floater 38 has no effect on the coarse motion arm 10 and will simply result in the corresponding scaled motion of the slave floater 40. If the master floater 38 position relative to the master stator 30 is outside of this deadband the computer 110 is programmed so that when the arm 10 is in the active mode the arm 10 tracks the movement of the master. Preferably a sole centring drift will be applied to the arm 10 tending to position the arm 10 relative to the master so that the arm 10 will always tend to be in the centre of the workspace of the master floater 38.

The central processing unit 110 converts the signals and the programmed input to an output that is directed back to the master and slave controls 200 and 300 and when programming is used to program the coarse movement back to the control 100. As illustrated, the control for the coarse movement 100 includes a motor controller for the transport boom as indicated at 116.

The voltage controlled current drivers 118 are used to drive the coils in the master and wrist as follows.

The position of the master floater 38 is sensed and this position is then duplicated in the slave floater 40 by control of the floater coils 50 of the slave 36. The reverse will also apply i.e. the master will track the movement of the slave. However, the degree of movement of the slave floater 40 will be significantly smaller than the degree of movement imparted to the master as described above based on the programmed value of the scaling factor. Thus, the control coils 50 in the slave 36 will be activated to move the floater 40 of the slave in essentially the same manner or direction as the master is moved but in increments that are significantly smaller than the increments of movement imparted to the master 32 or vice versa.

In addition the force feedback directly available as a result of the "coordinated motion" of the slave and master the forces sensed by the slave 36 (sensor 43) can be converted by the central processing unit 110 into signals for the voltage-controlled current drivers 118 for of the master control coils 202 to drive the master .floater 38 to apply an additional feedback force to the operator significantly larger than the force applied to the slave i.e. the force required to be applied by the operator to the master floater 38 to displace the floater 38 will be dependent on the forces required to be overcome in moving the tool 42 magnified to a preselected degree.

The computer 110 may also be programmed to guidance controls as indicated by the block 112. This control applies supplemental voltages to the coils 50 of the master 32 so that movement of the master out of a pre-programmed path is resisted by increasing the feedback forces when the operator attempts to move the master along a course other than that predefined by the computer 110, for example the tool 42 may be directed (via the supplemental preprogrammed forces applied to the master 32) to follow a selected course.

As example of the present invention, one would expect to build in to the master and slave, characteristics as indicated in Table 1.

conveyed to the master floater 38 from the slave floater 40 will be significantly high than the forces applied to the slave floater 40 base on the preset scaling factor described above.

When the movement of the master floater exceeds the above described deadband zone the moment of the master floater will also control the movement of the coarse movement arm 10.

As above indicated the position and force scaling can be programmed by the operator.

Having described the invention, modifications will be evident to those skilled in the art without departing from the scope of the invention as defined in the appended claims.

We claim:

1. A robotic system comprising an arm having a position adjustable-free end, said arm having joint connections constructed for macro-adjustments of said free end, an extension mounted on said free end, a micro teleoperation system mounted on said extension, said micro teleoperation system including a slave stator and a master stator mounted in fixed relationship on said extension, a slave floater cooperating with said slave stator and a master floater cooperating with said master stator, means for sensing the position of each of said master and said slave floaters relative to their respective said master and said slave stators, coupling means coupling said master floater and said slave floater so that movement of said master floater produces a scaled moment of said slave floater and movement of said slave floater produces a scaled movement of said master floater, said movement of said master resulting in a smaller corresponding scaled movement of said slave floater and said movement of said slave resulting in larger corresponding scaled movement of said master floater.

2. A robotic system as defined in claim 1 wherein said coupling means includes a programable computer means to scale said corresponding scaled movements of said master and slave floaters in accordance with a selected program.

3. A robotic system as defined in claim 1 further comprising means for sensing forces applied to said slave floater from its environment.

TABLE 1

|  | Master Characteristics | Slave Characteristics |
|---|---|---|
| Floater Mass | ≦500 grams | ≦50 grams |
| Maximum Continuous Force | ≧10 N | ≧2 N |
| Peak Force | ≧40 N | ≧8 N |
| Motion Range | ±4 mm translation | ±2 mm translation |
|  | ±5 deg. rotation | ±5 deg. rotation |
| Position Resolution |  | ≦0.25 μm |
| Force Resolution |  | ≦0.005 N |
| Position Frequency Response Bandwidth (without added load) | ≧10 Hz | ≧20 Hz |

While the Table 1 provides a good example, obvious modification could easily be made and the desired results still obtained.

In operation, the surgeon will simply grasp the master 32 and manipulate the master floater 38 which in turn will manipulate the slave floater 40 but with a degree of movement significantly less than the movement applied to the master. Forces applied to the master to produce this movement will be significantly greater than the forces applied via the slave to the tool to be manipulated and the forces sensed by the slave. Similarly the forces 4. A robotic system as defined in claim 3 further comprising means for sensing forces applied to said master floater by its environment.

5. A robotic system as defined in claim 4 wherein said coupling means further comprise means for modifying sensed said slave and said master environment forces and means for applying said modified forces to said master and said slave floaters respectively.

6. A robotic system as defined in claim 4 wherein said coupling means includes a programable computer means to scale said corresponding movements of said master and said slave floaters and said sensed forces in accordance with a preselected program and wherein said motions and forces are implemented for transparency in accordance with appropriate programmed processing of said master and said slave floater positions and sensed slave and master environment forces.

7. A robotic system as defined in claim 1 wherein said computer means further comprises computer-assisted means for controlling the compliance of said master and/or slave floaters to guide the movement of said master and/or slave floaters.

8. A robotic system as defined in claim 4 wherein said computer means further comprises computer-assisted means for controlling the compliance of said master and/or slave floaters to guide the movement of said master and/or slave.

9. A robotic system as defined in claim 5 wherein said computer means further comprises computer-assisted means for controlling the compliance of said master and/or slave floaters to guide the movement of said master and/or slave floaters.

10. A robotic system as defined in claim 6 wherein said computer means further comprises computer-assisted means for controlling the compliance of said master and/or slave floaters to guide the movement of said master and/or slave floaters.

11. A robotic system as defined in claim 1 wherein said arm is back drivable and said computer means includes means to control the movement of said arm when the position of said master floater relative to said master stator is outside a selected deadband zone based on movement of said master floater.

12. A robotic system as defined in claim 3 wherein said arm is back drivable and said computer means includes means to control the movement of said arm when the position of said master floater relative to said master stator is outside a selected deadband zone based on movement of said master floater.

13. A robotic system as defined in claim 4 wherein said arm is back drivable and said computer means includes means to control the movement of said arm when the position of said master floater relative to said master stator is outside a selected deadband zone based on movement of said master floater.

14. A robotic system as defined in claim 5 wherein said arm is back drivable and said computer means includes means to control the movement of said arm when the position of said master floater relative to said master stator is outside a selected deadband zone based on movement of said master floater.

15. A robotic system as defined in claim 6 wherein said arm is back drivable and said computer means includes means to control the movement of said arm when the position of said master floater relative to said master stator is outside a selected deadband zone based on movement of said master floater.

16. A robotic system as defined in claim 7 wherein said arm is back drivable and said computer means includes means to control the movement of said arm when the position of said master floater relative to said master stator is outside a selected deadband zone based on movement of said master floater.

17. A robotic system as defined in claim 8 wherein said arm is back drivable and said computer means includes means to control the movement of said arm when the position of said master floater relative to said master stator is outside a selected deadband zone based on movement of said master floater.

18. A robotic system as defined in claim 9 wherein said arm is back drivable and said computer means includes means to control the movement of said arm when the position of said master floater relative to said master stator is outside a selected deadband zone based on movement of said master floater.

19. A robotic system as defined in claim 10 wherein said arm is back drivable and said computer means includes means to control the movement of said arm when the position of said master floater relative to said master stator is outside a selected deadband zone based on movement of said master floater.

* * * * *